(12) United States Patent
Baur

(10) Patent No.: US 6,566,136 B2
(45) Date of Patent: *May 20, 2003

(54) IMMORTALIZED CELL LINE DERIVED FROM NORMAL HUMAN SKIN TISSUES

(75) Inventor: Markus Baur, Epalings (CH)

(73) Assignee: Nestec S.A., Vevey (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/663,645

(22) Filed: Sep. 18, 2000

(65) Prior Publication Data

US 2002/0042133 A1 Apr. 11, 2002

Related U.S. Application Data

(63) Continuation of application No. PCT/EP99/02347, filed on Apr. 7, 1999, which is a continuation-in-part of application No. 09/091,483, filed as application No. PCT/EP96/05812 on Dec. 19, 1996, now Pat. No. 6,423,540.

(30) Foreign Application Priority Data

Apr. 17, 1998 (EP) .............................. 98201247

(51) Int. Cl.[7] .............................................. C12N 15/87
(52) U.S. Cl. ..................... 435/467; 435/366; 435/325; 424/93.21
(58) Field of Search ................ 435/455, 7.23, 435/325, 320.1, 440, 467; 424/93.1, 93.21

(56) References Cited

U.S. PATENT DOCUMENTS 5,811,297 A * 9/1998 Gopal ..................... 435/320.1
6,197,585 B1 * 3/2001 Stringer ....................... 435/368

FOREIGN PATENT DOCUMENTS

WO  WO 97/23602  * 7/1997

OTHER PUBLICATIONS

Rhim, Neoplastic transformation of human cells in vitro, 1993, Critical Reviews in Oncogenesis, vol. 4, pp. 313–335.*

Boukamp et al., Normal keratinization in a spontaneously immortalized aneuploid human keratinocyte cell line, 1988, The Journal of Cell Biology, vol. 106, pp. 761–771.*

Pearson et al., The genetic analysis of cancer, 1998, Journal of Internal Medicine, vol. 243, pp. 413–417.*

Ngo et al., Computational complexity, protein structure prediction, and the levinthal paradox, 1994, The Protein Folding Problem and Teritary Structure Prediction, pp. 491–494.*

Agarwal et al., Immortalization of human keratinocytes by simian virus 40 large–T–antigen alters keratin gene response to retinoids, 1990, Cancer Research, vol. 50, pp. 5947–5953.*

Richard L. Eckert et al., "Cloning of cDNAs specifiying vitamin A–responsive human keratins", Proc. Natl. Acad. Sci. USA, vol. 81, pp. 4321–4325, (1984).

Mils V et al., "1, 25–Dihydroxyvitamin De and its synthetic derivatives MC903 and EB1089 induce a partial tumoral phenotype reversal in a skin–equivalent system." J Investig Dermatol Symp Proc. (Apr. 1996) 1 (1) 87–93, Journal Code: COU. ISSN: 1087–0024., XP002077498, p. 87.

Tinois et al. "Growth and Diferentiation of Human Keratinocytes on Extracellular Matrix", Archives of Dermatological Research, vol. 279, No. 4, 1987, pp. 241–2466, XP002077499, p. 241.

* cited by examiner

Primary Examiner—Dave T. Nguyen
Assistant Examiner—Brian Whiteman
(74) Attorney, Agent, or Firm—Winston & Strawn

(57) ABSTRACT

A human keratinocyte cell line immortalized by at least one functional tumor gene of DNA viral origin characterized in that it is: (1) non-tumorigenic, (2) conserves the capacity for differentiation and for the expression of proteins and of enzymes expressed by normal differentiated keratinocytes even after an elevated number of passages in culture; and (3) forms a stratified and polarized epithelium having a stratum corneum ortho-keratinocyte, if cultivated in an organotypical culture in a medium without serum and without a layer of nourishing cells. An improved process to immortalize human skin cells to obtain immortalized keratinocytes. Also, the use of keratinocytes for immunological, pharmacological, photo- and chemical-toxicological analyzes of skin reaction and for expression of heterologous genes and for the construction of artificial skin.

12 Claims, 2 Drawing Sheets

IMMORTALIZED CELL LINE DERIVED FROM NORMAL HUMAN SKIN TISSUES

This application is a continuation of U.S. national phase designation of copending PCT application PCT/EP99/02347 filed on Apr. 7, 1999, which is a continuation-in-part of U.S. patent application Ser. No. 09/091,483 filed on Jun. 19, 1998, U.S. Pat. No. 6,423,540, which is a 371 of PCT/EP96/05812 filed Dec. 19, 1996.

The present invention relates to new immortalised cell lines derived from normal human skin tissues and presenting improved differentiation characteristics, to a new method for producing these cell lines and to various usages thereof, particularly in the field of creating artificial skin.

STATE OF THE ART

The production of immortalised cell lines derived from normal human skin tissues has already been described. In general, the processes used for this purpose comprise transformation of human skin cells, for example of keratinocytes and melanocytes, which are cultivated in vitro with agents conveying immortalization. Immortalization relates to the production of cells, which may be cultivated during prolonged period of times in vitro, theoretically for an indefinite period. These cells are also designated continuous cell lines. In contrast thereto, the non-immortalised cells are only capable to proliferate during a defined number of cell divisions in vitro. The immortalised cells are extremely advantageous, since they provide a stable, potentially unlimited source of cells having defined characteristics. Typical agents for the production of immortalised cell lines and of immortalised human skin cell lines comprising in particular, for example viruses, recombinant viruses and plasmids containing DNA sequences conveying the property of immortalization.

The most common process for producing immortalised human cell lines comprises probably the use of sequences of the Simian Virus 40 (SV 40) and more specifically of the DNA of the large T antigen (T-Ag) of SV40 as the agent of immortalization. For example, Steinberg et al., J. Cell Phys, 123, 117–125 (1985); U.S. Pat. No. 4,885,238 (Reddel et al.); U.S. Pat. No. 4,707,448 (Major); Stoner et al., Cancer Res., 51, 365–371 (1991); Chopra et al., In vitro Cell Dev. Biol., 30A, 539–546 (1994); Chopra et al., In vitro Cell Dev. Biol., 27A, 763–765 (1991); Christian et al., Cancer Res., 47, 6066–6073 (1987); Rhim et al., Science, 227, 1250–1252 (1985); and Grubman et al., Gastroint. Liver Physiol., 29, G1060–G1070 (1994) report of the use of SV40 vectors and of vectors containing the sequence of the large T antigen of SV40 for producing immortalised human cell lines. The introduction of such sequences is generally effected by infection with the SV40 virus or with a 12/SV40 hybrid-adenovirus or by transfection of cells with a recombinant plasmid containing the long terminal repeats of the Rous sarcoma virus and the regulatory SV40 ori-region by coprecepitation in the presence of strontium phosphate (see Brash et al., Mol. Cell Biol.,7, 2031–2034, 1987).

Another known process for the production of immortalised cell lines and in particular of immortalised human keratinocytes comprises the transfection or infection of cells with DNA sequences of the human papilloma virus (HPV). For example, U.S. Pat. No. 5,376,542 (Schlegel) describes the immortalization of human epithelial cells with the E6 and E7 genes isolated of HPV-16, 18, 31, 33 or 35 or with the E7 gene alone for producing non-tumorigenic immortalised human cell lines. Moreover, Barbosa et al. Oncogene, 4, 1529–1532 (1989); and Münger et al. J. Virol., 63(10): 4417–4421 (1989) report of the use of the E6 and E7 genes of HPV-16 and HPV-18 for producing immortalised human keratinocytes. Moreover, Dürst et al., Oncogene, 1, 251–256 (1987) describes the immortalization of keratinocytes with the papilloma virus type 16.

Nevertheless, although numerous groups described immortalized keratinocyte cell lines and their use in in vitro assays, the immortalized keratinocyte cell lines of the state of the art present usually one or more properties rendering their utilization disadvantageous. For example, the previously described immortalized keratinocytes present one or more of the following properties: (i) reduction or loss of expression of differentiation markers, for example of proteins being expressed by normal differentiated keratinocytes, (ii) properties of modified growth in culture of tissues and (iii) formation of a stratified and polarized epithelium having a stratum corneum para-keratinocyte.

In order to eliminate these disadvantages, EP780469 (Société des Produits Nestlé) proposes a new method for immortalizing keratinocytes or human melanocytes using en sus a new culture medium, the vector pLXSHD+SV40 (#328), which is derived from SV40 virus, or equally the vector pLXSHD+E6/E7, which is derived from the human papilloma virus 16 (HPV-16). The immortalized cells obtained in this way preserve the capacity of differentiation and of expression of proteins and of enzymes, which are expressed by normal differentiated keratinocytes and melanocytes, even after an elevated number of passages in culture.

However, in spite of the previous descriptions, there is still an important need in the practical field to have human immortalised keratinocytes possessing even more ameliorated properties. Such cells would be extremely advantageous for numerous uses, particularly for analyses needing highly differentiated skin cells.

SUMMARY OF THE INVENTION

For this purpose, the present invention relates to a human immortalized keratinocyte cell line by means of at least one tumorgenic functional gene of DNA viral origin, which is characterized in that it:

(1) is non-tumorigenic, (2) conserves the capacity to differentiate and to express proteins and enzymes expressed by normal differentiated keratinocytes after an elevated number of passages in tissue culture, and (3) forms a stratified and polarised epithelium having a stratum corneum ortho-keratinocyte, if cultivated in organo-typical culture in a serum-free medium and without a layer of nourishing cells.

Another object of the present invention is to provide a new process for producing immortalised keratinocyte cell lines derived from normal skin tissues.

Yet, another object of the present invention is to provide processes for the use of these keratinocyte cell lines according to the invention, for example for immunological, pharmacological, photo- and chemical-toxological analyses of skin reaction, and for the expression of heterologous genes.

DETAILED DESCRIPTION OF THE INVENTION

Figure 1:
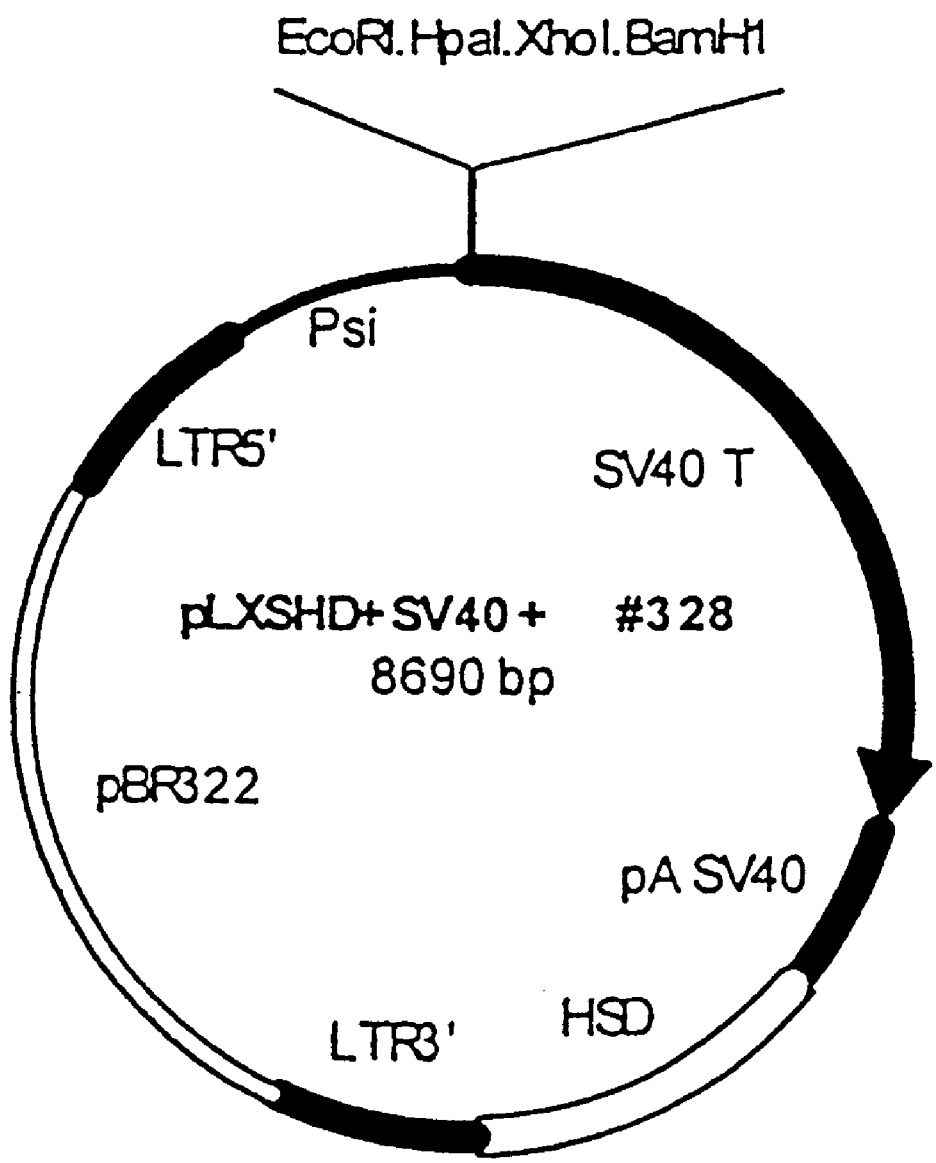
FIG. 1 shows the retroviral construct having a tumor gene from virus SV40, namely the plasmid pLXSHD+SV40 (#328) used for immortalizing the keratinocytes of the present invention.

The present invention provides non-tumorigenic, immortalised keratinocyte cell lines, that is cell lines that do not form tumors when injected under the skin of an animal using at least $2 \times 10^6$ cells for each injection, for example.

These cell lines also conserve the capacity to differentiate and to express proteins of differentiation expressed by normal keratinocytes after a an elevated number of passages. The expression "elevated number of passages" indicates at least 10 passages in culture, preferably at least 20 to 30 passages, more preferably at least 50 passages and theoretically an unlimited number of passages. For example, the immortalised keratinocytes produced according to the present invention express the differentiation proteins consisting of keratin K1/10, keratin K14, involucrine, filaggrine and loricrine even after a an elevated number of passages in culture of tissues.

The immortalised keratinocytes of the present invention have a profile of cytochrome p450 (CYP450) which is similar to, if not identical, to the profile of normal keratinocytes. For example, the cells of the present invention express CYP450 1A1, 2E1, 2C18 and 3A5. Moreover, the immortalised keratinocytes of the present invention express enzymes of phase II, for example glutathion-S-transferase $\pi$ (GST$\pi$), in a way comparable to normal, non-immortalised keratinocytes.

Moreover, the immortalised keratinocytes of the present invention express proteins and enzymes implicated in the cell oxidation and in inflammatory responses, for example the superoxyd-dismutase (SOD) and the collagenase of type I and the tumor necrosis factor alpha (TNF$\alpha$) after treatment with phorbol-esters, in a way similar or identical to the way of normal differentiated keratinocytes. With these given characteristics, these cell lines represent an extremely interesting, reproducible source for immunological, pharmacological, inflammatory, photo- and chemical-toxicological studies of skin reactions.

Moreover, the lines of immortalised keratinocytes of the present invention form, if cultivated in organotypical culture in serum-free medium [for example the medium NR2 of Biofluids Inc., U.S., enriched with EGF (5 ng/ml), vitamin C (38 $\mu$g/ml) and CaCl$_2$ (1,5 mM)] and without a layer of nourishing cells (without fibroblasts), a stratified and polarised epithelium having superficial keratinized layers, the ordinarily so-called stratum corneum having an ortho-keratinocyte morphology, which means that the stratum corneum is deprived of nuclear cells, i.e. cells containing nuclei.

The preparation of a stratified and polarised epithelium with immortalised keratinocytes was previously achieved under classic culture conditions, i. e. by a technique using a medium containing calf serum and a layer of nourishing cells (Lechner et al., Virology, 185, 536–571,1991). Nevertheless, the immortalised cells did not form the normal superficial keratinized layers. For example, the cell lines immortalised by papilloma virus 16 or 18, or E6/E7, are known to form very disorganised epithelia (Blanton et al., Am. J. Pathol., 138, 673–685, 1991; Hudson et al., J. Virol., 64, 519–526, 1990; McCane et al., Proc. Natl. Acad. Sci., 85, 7169–7173, 1988; Woodworth et al., Oncogene,7, 619–626, 1992).

In contrast thereto, the lines described in EP780469 (Société des Produits Nestlé), if cultivated in organo-typical culture in a serum-free medium and without a layer of nourishing cells, formed a stratified and polarized epithelium having normal superficial keratinized layers, but having nevertheless a para-keratinocyte morphology, that is, the stratum corneum contained still cell with nuclei.

The immortalised keratinocytes of the present invention also absorb exogenous essential fatty acids (AGE) and present a unsaturated state and a prolongation of the chain of the AGE perfectly corresponding to the unsaturated state and prolongation of the chain of normal keratinocytes.

In general, the immortalised keratinocytes of the present invention may be obtained according to the following process:

(i) obtaining a sample of human skin;

(ii) preparing the sample of skin in order to obtain primary keratinocytes able to be cultured;

(iii) culturing these primary keratinocytes in a serum-free medium, preferably in the medium NR-3 (described in EP780469) on culture plates having a coating facilitating the fixation and the growth of cells, said coating comprising fibronectin, SAB and collagen of type I; replacing the serum-free medium in a way sufficient to obtain an optional confluent growth of keratinocytes on the culture plates, the coating of the plate being maintained in a continuous way;

(v) separating keratinocytes in culture from melanocytes and transferring the separated keratinocytes into an infection medium, preferably into the medium NR-3, and preferably after treatment of the cells with a composition containing trypsin and EDTA using culture plates coated in a similar way;

(vi) infecting cells with functional tumorigenic genes of at least two different DNA viruses, such as the SV40 virus and the human papilloma virus;

(vii) transferring immortalized keratinocytes into a proliferation medium without serum to culture plates coated beforehand in a similar way, preferably into the media NR-2 or NR-3 (media described in EP780469, which composition is incorporated herein by way of reference); and (viii) transferring immortalized keratinocytes after proliferation into a convenient differentiation medium having a high content of calcium (1.5 mM), preferably into the medium NR-2 enriched with EGF (5 ng/ml) and vitamin C (38 $\mu$g/ml).

In details the step (i) usually comprises obtaining samples of human skin tissue of normal human donors, for example samples obtained during a surgical intervention or a pediatric intervention. The immortalization of a unique sample of skin cells, i.e. of an autologous sample of skin cells, permits the production of immortalised keratinocyte cell lines presenting defined characteristics, for example a profile of a particular receptor being characteristic for a particular donor.

The sample of skin tissue is subsequently prepared in step (ii) such that it is suitable for an in vitro culture. This preparation is preferably effected by initially washing the sample of skin tissue, for example using the medium utilized for the culture. Preferably, this operation is performed in the medium NR-2, which is a serum-free medium, the exact composition of which is described in EP780469, which showed to be advantageous for the culture of normal keratinocytes. After washing, the sample of skin tissue is preferably shaved, for example by the mean of a dermatom, and is subsequently cut into small pieces.

The resulting sections of skin are then preferably separated in dermis and epidermis. This may be achieved by physical and/or enzymatic means. For example, this may be realised by treatment with trypsin, for example by flotation of the samples of skin tissue in a trypsin solution (for example about 0.5%) containing EDTA (for example about 0.1%) during a time sufficient to provoke cell separation, for example during a time of about 30 to 60 minutes at a temperature of 37° C., or for example during night at 4° C.

The dermis is separated and the epidermis is subsequently placed in a medium for achieving a suspension. Preferably, the medium for achieving a suspension contains a solution of soy trypsin inhibitor (SBTI) and is put in contact with the cells for a time sufficient, usually of about 5 minutes, to inactivate the trypsin and to provoke the release of the cells. A tissue culture medium, preferably the medium NR-2, deprived of serum (described in EP780469, and a filter (for example a filter of 100 nm) are subsequently added in order to obtain the desired cells, i.e. the keratinocytes.

The resulting primary kerationcytes obtained in step (ii) are subsequently used to seed a serum-free medium, preferably the medium NR-3 (described in EP780469, in a suitable cell concentration, preferably of about $1.2 \times 10^4$ cells/cm$^2$, on previously coated culture plates. However, it is possible to vary this concentration of cells within wide limits. The culture plates are preferably provided with a coating containing a composition which proved to increase fixation and the growth of keratinocytes, more precisely a solution of fibronectin, of SAB and of collagen type I.

In step (iv), the culture medium is replaced as often as necessary in order to obtain an optimal cell growth. Preferably, the medium is replaced each time after about two days. However, this is variable depending on the particular sample of skin tissue. After having obtained a nearly total confluence, for example a confluence of about 90%, what takes place after a time period of about 10 to 14 days, the keratinocytes and the melanocytes are separated. This may be realised by any chosen means allowing for an adequate cell separation without any detrimental effect on the melanocytes and the keratinocytes. For example, this may be effected by a differential treatment with trypsin. Preferably, the melanocytes or keratinocytes are treated with a trypsine/EDTA solution and are subsequently transferred into a selection medium. In the case of keratinocytes, the cells are preferably treated during a time period of about 5 to 10 minutes with a solution of trypsine/EDTA (0.025%/0.01%) and are subsequently used in step (v) to be sown into medium NR-3 on previously coated plates.

Figure 2:
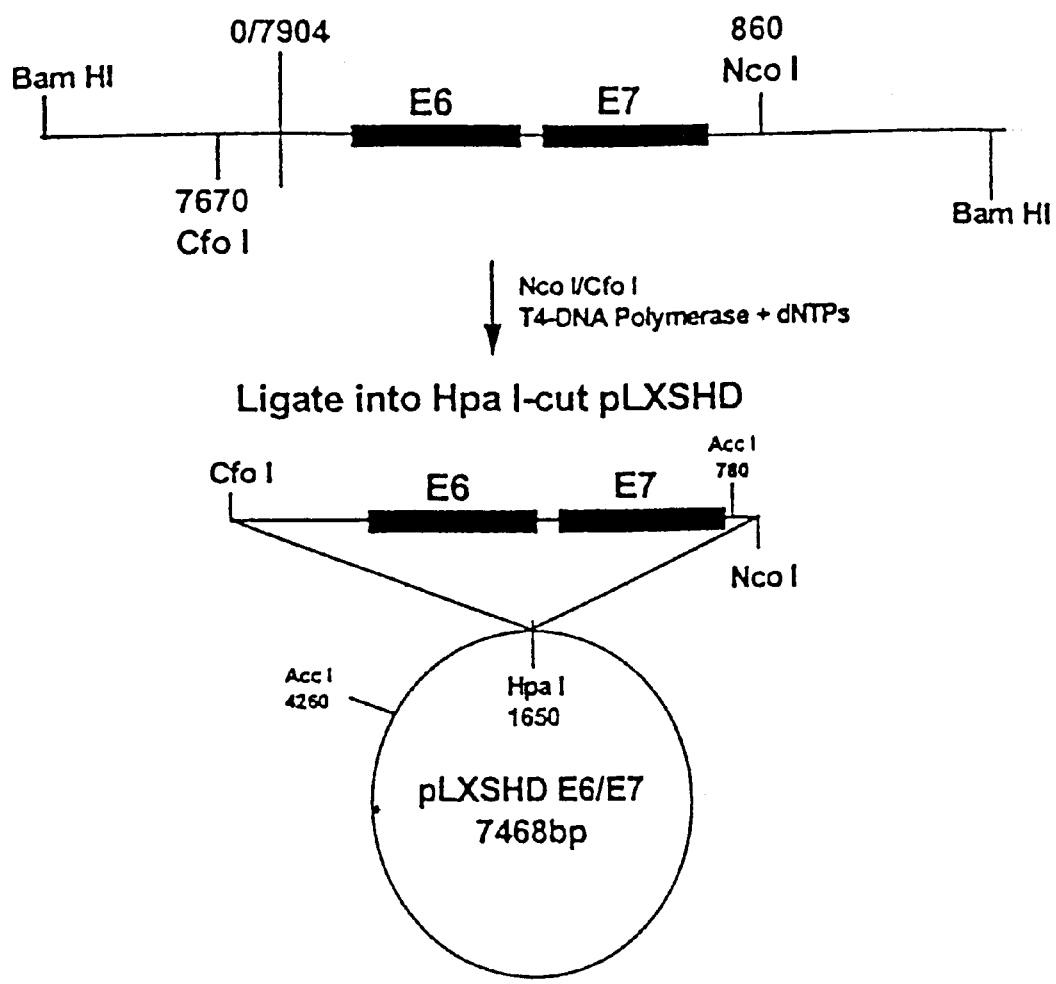
FIG. 2 represents the retroviral construct having a tumor gene from the papilloma virus 16, namely the plasmid pLXSHD+E6/E7 used for immortalizing the keratinocytes of the present invention.

The keratinocytes are subsequently treated with an agent for immortalization. The cells may also be frozen until the immortalization is effected, for example in liquid nitrogen. The infection and immoralization are preferably effected by using functional tumorigenic genes of at least two different DNA viruses, such as the T-Ag of SV40 virus and the E6/E7 of HPV16. Each of these genes may be present in an independent retroviral construct, for example in the vector pLXSHD+SV40(#328), shown in FIG. 1 and described by Stockshaelder et al. (GeneBank, accession number M64753; Human Gen. Therapy, 2,33–39, 1991) and the vector pLXSHD+E6/E7, which is shown in FIG. 2.

The retroviral vector pLXSHD+SV40(#328) contains among other sequences the T-Ag sequence of SV40, the sequences the 5' and 3' long, terminal repeats of SV40, the sequences of pBR322, which allow for the replication of *E. coli,* a cycle of multiple cloning, a polyadenylation sequence of SV40.

At the location of the gene coding for the T antigen the vector pLXSHD+E6/E7 contains the NcoI/CfoI fragment of the E6/E7 gene derived from the human papilloma virus 16.

After the immortalisation, the cells are subsequently submitted to the necessary number of passages during culture and the resulting immortalised cells are subsequently transferred into a proliferation medium during step (vii). This transfer is preferably effected during the second passage. This proliferation medium may be a serum-free medium, preferably the medium NR-2 or NR-3. The immortalised cells are cultivated on culture plates previously coated in a continuous manner, the coating comprising again a solution of fibronectin, of SAB and of collagen type 1.

After multiplication of immortalized cells in a proliferation medium (preferably NR-2) the keratinocytes are transferred in step (viii) into an environment provoking the differentiation of normal and immortalized keratinocytes, preferably into an environment simulating the conditions prevailing in the skin, thus generating the organization of keratinocytes in a stratified and polarized epithelium having normal, superficial keratinized layers. To this end, the cells may be cultivated in a serum-free medium having a high content of calcium, such as the medium NR-2 comprising about 1.5 mM or calcium, about 5 ng/ml of EGF and about 38 $\mu$g/ml of vitamin C, the culture being effected on plates during 2 to 3 weeks at liquid air interphase, for example on plates with 12 cavities Falcon No. 3043, each cavity having an insert Falcon No. 3180 wherein the keratinocytes are developing at the air/liquid interphase. The air consists of the atmosphere contained in the internal space of the insert, which is deprived of nourishing medium. The liquid is the nourishing medium contained in the cavity, the medium traversing the membrane of the insert on which the keratinocytes are developing.

With regard to the properties of immortalized keratinocytes of the present invention, these are perfectly suitable for immunological, pharmacological, photo- and chemical-toxological analyses of skin reactions. For example, the immortalized keratinocyte cell lines of the present invention may be used for analyses requiring differentiated skin cells, for example studies on the barrier function (keratinization) of reconstructed skin tissue, studies on the metabolism of differentiated keratinocytes (metabolism of fatty acids, anti-oxidant metabolism), studies concerning the effects of UV irradiation on skin cells, studies concerning the effects of potential skin irritating and skin sensibiliating agents on skin cells, studies on lipid metabolism, local treatment and/or by medium with xenobiotic agents (for example cosmetic oils, by selecting feasible protective compounds, for example photo-protective agents), studies on inflammation and on skin irritation, etc.

Moreover, the of keratinocyte cell lines produced according to the present invention are used to select potential anti-cancer compounds and potential compounds for the treatment of skin diseases. This usually implies that the cell line is contacted with such compounds during a given time period and the determination of a potential induction of detrimental effects whatsoever, for example genotoxicity, the formation of DNA-adducts, mutagenicity, cellular transformation or cytotoxicity.

Moreover, the lines of immortalised keratinocytes of the present invention may be used in DNA mutagenicity assays, assays for the selection of skin mutagenic agents, assays for the identification of agents of alteration of chromosomes, studies on malignant transformation, studies on cellular biochemistry (for example assays of the activation of CYP450), the selection of compounds and of compositions, for example of cocktails of essential fatty acids, involved in inflammatory and allergic reactions, assays for the activation of collagenase (in connection with inflammation), involving TNF$\alpha$, and the detection of interleukine.

With respect to the fact, that the cell lines according to the present invention form a stratum corneum ortho-keratinocyte, they are particularly well adapted to participate in the preparation of artificial skin, to be intended for studies on mutagenicity, for immunological, pharmacological, photo- and chemical-toxological studies, mentioned above. This skin may be constituted only of an epithelium of keratinocytes according to the invention, but preferably comprises also collagen, fibroblasts, even melanocytes, in order to achieve a better resemblance to normal human skin, for example.

Moreover, the keratinocyte cell lines of the present invention are capable to express recombinant proteins, for example human polypeptides and proteins and also to produce RNA and DNA.

Among the immortalized keratinocyte cell lines produced according to the present invention, only the cell line DK7-NR was deposited under the terms of the Treaty of Budapest, as an example, on Mar. 19, 1998 at Collection Nationale de Culture de Microorganisme (C.N.C.M) having the address 25, rue de Docteur Roux, 75724 Paris, France, and has received the deposit number CNCM I-1996. This deposit was effected under the terms of the Budapest Treaty. All restrictions concerning the availability of this cell line will be irrevocably lifted after the grant of a patent corresponding to the present application or another application claiming the right of priority of this application.

Other characteristics of the present invention will become apparent from the following description of examples, which are given for illustrating the present inventionand should not be construed to be limiting. When not indicated otherwise, the manipulation of cells, the preparation of vectors, the transformation of cells and all other technical processes are performed according to the protocols described in the publication of Sambrook et al. (Molecular Cloning, A Laboratory Manual, Cold Spring Harbor Laboratory Press, USA, 1989).

EXAMPLE 1

Preparation and Characterisation of Cell Lines

Breast skin tissues are taken. After separation of the dermical and the epidermical part, the dermis is cut into small pieces of 0.2×0.2 mm and is fixed on a culture plate of 6 cm with serum. Minimal essential medium of Dulbecco (DMEM, 10% of fetal calf serum) is added after 2 to 4 hours. This culture of explant is subsequently incubated until an excessive growth of fibroblasts becomes visible. The cultures of confluent fibroblasts are separated and multiplied in order to obtain frozen reserve cultures.

Culture boxes are seeded with primary cells coated in a continuous manner with a "cocktail" coating previously described for bronchial cells (Lechner et al., J. Tiss. Cult. Meth., 9:43–49 (1985)). After achieving a nearly total confluence, for example about 90% of confluence, which occurs usually after a time period of about 10 to 14 days, the keratinocytes and the melanocytes are separated. To this end, the culture is treated with a solution of trypsine/EDTA (0,025%/0,01%) during 5 min, and the melanocytes are subsequently harvested which separated themselves first from the keratinocytes. The primary keratinocytes are subsequently cultivated up to the desired number of cells, in the medium NR-3 without serum, by means of the described coated culture boxes (the medium NR-3 favours the growth of keratinocytes in comparison to the melanocytes).

Subsequently, the cells of encapsulation "packaging cell line 3T3-fibroblasts" are transfected with the plasmides pLXSHD+SV40(#328) and pLXSHD+E6/E7 according to the protocol of Pfeifer et al. (Meth. Cell Sci., 17, 83–89, 1995) with the proviso, that the virus is collected after encapsulation in a cell line, that grows in DMEM medium with 10% with fetal bovine serum. Subsequently, the keratinocytes are infected with the virus in order to bring about immortalization. During the infection, the medium without serum PC-1, which is described in the publication of Pfeifer et al., is used as well.

After the immortalization, the immortalised keratinocytes are transferred into the proliferation medium NR-2 or NR-3, using previously coated culture boxes. After proliferation of the cells up to a desired number of cells, the cells are transferred into a differentiation medium suitable for the culture of normal and immortalised keratinocytes (NR-2).

It can be shown that the immortalized keratinocytes present an ameliorated cell growth at an elevated number of passages in culture, which may be compared to those described for the cell lines of EP780469.

The expression of CYP450, 1A1, 1A2, 3A5, 2E1, 2B6, 2A6 and 2D6 is analyzed in skin cells consisting of normal and immortalised keratinocytes by DNA polymerase chain reaction at room temperature (expression of mRNA,). The profile of CYP450 expressed by immortalised keratinocytes is particularly similar, even identical, to that of normal keratinocytes.

The cell lines respond to the inducing agent of CYP450 consisting of benz(a)pyrene in the same manner as do the non immortalized cells even at an elevated number of passages.

The differentiation markers are analysed by means of specific antibodies against the T-Ag, involucrine, filaggrine, loricrine, vimentine and the keratins K4, K7, K8, K10/1, K13, K14, K17, K18 and K19. The best capacity for the demonstration of the capacity of differentiation could be demonstrated for the cell line DK7-NR.

The glutathion-S-transferase (GST) is analyzed by Western-Blot and Northern-Blot. All lines of keratinocytes express strongly the messenger RNA for GSTπ. The profile of exposition to GSTα, GSTμ and GSTπ in the cell lines is similar to that of normal keratinocytes.

In order to analyze and to compare the desaturation and the elongation of the added AGE to keratinocytes, the immortalized keratinocytes (and normal keratinocytes) are treated with linoleic acid (LA, 15 μmole) and linolenic acid (LN, 15 μmole). For these experiments, the medium NR-2 (Biofluids Inc.), deficient in AEG, is used. The cell cultures are treated after having reached confluence and are transferred from the medium into a NR-2 medium having a high content of calcium (1.5 mM). The cells are treated during 4 days with the AGEs (renewed after 2 days). The analysis of the AGE is effectuated by extraction and separation of the phospholipids by CCM (thin layer chromatography) and the quantification of the methyl esters of the fatty acids is effected by CGL (Chromatography Gas-Liquid). The formation of the desaturation and of the elongation of LA (20:4n-6 and 22:4n6) and of LN (20"5n-3, 22:5n-3 and 22:6n-3) could be shown. The metabolic profile was consistent with that observed with normal keratinocytes.

All cell lines were hypodiploid with most of the counts of chromosomes in the interval of diploid cells. Apart from the analysed cells no other cells were detected in the cultures. This result confirms the purity of the cell lines and the absence of any contamination originated from other sources.

The tumorigeneicity of the immortalised keratinocytes is determined by subcutaneous injection (1–2 $10^6$ keratinocytes) to nude mice. The lines of the tested keratinocytes and particularly of the line DK-7-NR are not tumorigenic in nude mice.

EXAMPLE 2

Preparation of an Epithelium

The medium NR2 containing 750,000 cells of a cell line according example 1 is prepared, 0.5 ml of this medium is put in the inserts Falcon No. 3180, they are placed in the cavities of the plates Falcon No. 3043 containing already 2 ml of fresh medium NR-2, the keratinocytes are cultivated during 2 days under conditions favorable for the growth of the keratinocytes. On the third day the medium contained in the insert is removed and the cells are left at free air. The medium contained in the cavities is periodically changed each 2 days with medium NR-2 supplemented with EGF (5 ng/ml), vitamin C (38 $\mu$/ml) and $CaCl_2$ (1.5 mM). After 2 to 3 weeks in culture at the interphase air-liquid, the epithelium formed in that way is collected, fixed with picric acid and the morphology is analyzed.

The results show that the keratinocyte cell lines, in particular the cell line DK7-NR, form a stratified and polarized epithelium, the commonly so-called stratum basale, containing cells having a cuboidal morphology identical to that of normal cells. The stratum corneum presents a morphology ortho-keratinocyte, that is it is deprived of cells containing a nucleus. The formation of the ortho-keratinocyte cell layer was not possible with other known immortalized cell lines up to this day. For example, under identical conditions the line DK2NR (EP780469) forms a stratum corneum para-keratinocyte, that is the layer of cornified cells still contains cells with a nucleus. Only the morphology ortho-keratinocyte of the stratum corneum reflects the normal situation of human skin. In fact, the stratum corneum para-keratinocyte is characterized by a anormal hypertrophy of the epithelium leading to disorders, such as psoriasis or neophasia, for example.

EXAMPLE 3

Irritation Test

The cell lines obtained in example 1, in particular the line DK7-NR, are cultivated in the medium NR-2. The induction of the "stress gene" TNF$\alpha$ (tumor necrosis factor alpha) after treatment with skin irritating agents, consisting of PMA (Phorbol-12-myristate-13-acetate) and of UV-B (ultraviolet B irradiation) is analyzed by the Northern method and by biological assays. The results show that the cell lines and particularly the cell line DK7-NR respond to PMA and to UV-B and express the protein TNF$\alpha$ even after an elevated number of passages.

EXAMPLE 4

Construction of Artificial Skin

The membrane of an insert Falcon No. 3180 is replaced by a sheet of the benzylic ester of hyaluronic acid (Hyaff 11). The bottom of the insert is seeded with primary human fibroblasts ($0.1 \times 10^6$ cells in 0.2 ml medium), after 30 min in repose, the insert is filled with the medium DMEM containing 10% fetal calf serum, incubation is performed at 37° C. under an atmosphere containing 5% of carbon dioxide during several days, the insert is emptied and 0.5 ml of fresh medium NR-2 containing 750,000 cells of the cell line DK7-NR is supplied, the inserts are placed in the cavities of the plates Flacon-No. 3043 already containing 2 ml of fresh medium NR-2 and the cells are cultivated during 2 days under conditions favorable for the growth of the keratinocytes. On the third day, the medium contained in the insert is removed and the cells were left at the free air. The medium in the cavities is changed periodically every 2 days with medium NR-2 supplemented with EGF (5 ng/ml), vitamin C (38 $\mu$g/ml) and $CaCl_2$ (1.5 mM). After 2 to 3 weeks of culture in air-liquid interphase, the formation of artificial skin presenting the characteristics of normal skin can be observed.

What is claimed is:

1. A human keratinocyte cell line immortalized by transfecting with at least one retroviral construct comprising functional tumor genes E6/E7 of HPV16or the large T antigen from SV40, respectively.

2. The immortalized human keratinocyte cell line of claim 1, wherein the cell line has at least the following characteristics:
   (a) the cell line is non-tumorigenic;
   (b) the cell line conserves the capacity of differentiation and for the expression of proteins and of enzymes expressed by normal differentiated keratinocytes before and after an elevated number of passages in culture; and
   (c) the cell line forms a stratified and polarized epithelium having a stratum corneum orthokeratinocyte, when cultivated in an organo-typical culture in a media without serum and without a layer of nourishing cells.

3. A process for immortalizing human skin cells to obtain immortalized keratinocytes, comprising the following steps:
   (i) isolating a sample of human skin;
   (ii) preparing the sample of skin for in vitro culture;
   (iii) obtaining keratinocytes from the prepared sample of skin tissue and seeding a growth medium without serum with said keratinocytes, on culture plates provided with a coating comprising fibronectin, collagen type I and BSA, which facilitate the fixation and the growth of cells;
   (iv) replacing the medium in a way sufficient to obtain an optimal confluent growth of cells in culture, continuously maintaining the coating of the plate;
   (v) transferring keratinocytes to a selection medium without serum;
   (vi) transfecting keratinocytes with a first retroviral construct expressing the functional tumor E6/E7 genes and a second retroviral construct expressing the functional tumor large T antigen gene;
   (vii) transferring the resulting immortalized keratinocytes into a proliferation medium without serum suitable for the proliferation of immortalized keratinocytes; and
   transferring the resulting proliferated keratinocytes into a differentiation medium without serum having a high content of calcium.

4. A human keratinocyte cell line immortalized by transfecting with at least one retroviral construct comprising a functional tumor gene which is a functional large T antigen gene from SV40 virus or E6 or E7 gene from human papilloma virus 16, wherein the cell line has at least the following characteristics:
   (a) the cell line is non-tumorigenic;
   (b) the cell line conserves the capacity of differentiation and for the expression of proteins and of enzymes expressed by normal differentiated keratinocytes before and after an elevated number of passages in culture; and (c) the cell line forms a stratified and polarized epithelium having a stratum corneum orthokeratinocyte, when cultivated in an organo-typical culture in a media without serum and without a layer of nourishing cells.

5. The human keratinocyte cell line according to claim 4, wherein the retroviral construct comprises both E6 and E7 from human papilloma virus 16.

6. Artificial skin, comprising the keratinocyte cell line according to claim 5.

7. Artificial skin, comprising the keratinocyte cell line according to claim 4.

8. The cell line DK7-NR having the deposit number according to the treaty of Budapest CNCM I-1996.

9. Artificial skin, comprising the keratinocyte cell line according to claim 8.

10. A process for immortalizing human skin cells to obtain immortalized keratinocytes, comprising the following steps:

(i) isolating a sample of human skin;

(ii) preparing the sample of skin for in vitro culture;

(iii) obtaining keratinocytes from the prepared sample of skin tissue and seeding a growth medium without serum with said keratinocytes, on culture plates provided with a coating comprising fibronectin, collagen type I and BSA, which facilitates the fixation and the growth of cells;

(iv) replacing the medium in a way sufficient to obtain an optimal confluent growth of cells in culture, continuously maintaining the coating of the plate;

(v) transferring keratinocytes to a selection medium without serum;

(vi) transfecting keratinocytes with a retroviral construct comprising a functional tumor gene which is functional large T antigen gene from SV40 virus or E6 or E7 gene from human papilloma virus 16;

(vii) transferring the resulting immortalized keratinocytes into a proliferation medium without serum suitable for the proliferation of immortalized keratinocytes; and (viii) transferring the resulting proliferated keratinocytes into a differentiation medium without serum having a high content of calcium.

11. The process of claim 10, wherein the retroviral construct comprises both E6 and E7 from human papilloma virus 16.

12. The process of claim 10, wherein the constructs comprise pLXSHD+SV40(#328) and pLXSHD+E6/E7.

* * * * *

UNITED STATES PATENT AND TRADEMARK OFFICE
CERTIFICATE OF CORRECTION

PATENT NO. : 6,566,136 B2
DATED : May 20, 2003
INVENTOR(S) : Baur

It is certified that error appears in the above-identified patent and that said Letters Patent is hereby corrected as shown below:

Column 10,
Line 15, change "HPV16or" to -- HPV16 or --.

Signed and Sealed this

Eighth Day of July, 2003

JAMES E. ROGAN
*Director of the United States Patent and Trademark Office*